US00RE36489E

United States Patent [19]

Alexay

[11] E Patent Number: Re. 36,489

[45] Reissued Date of Patent: Jan. 11, 2000

[54] SPECTRAL ANALYZER WITH NEW HIGH EFFICIENCY COLLECTION OPTICS AND METHOD OF USING SAME

[75] Inventor: Christopher C. Alexay, Walpole, N.H.

[73] Assignee: Janos Technology Inc., Townshend, Vt.

[21] Appl. No.: 08/877,603

[22] Filed: Jun. 18, 1997

Related U.S. Patent Documents

Reissue of:

[64] Patent No.: 5,428,222
Issued: Jun. 27, 1995
Appl. No.: 08/224,655
Filed: Apr. 6, 1994

[51] Int. Cl.[7] ..... G01N 21/01

[52] U.S. Cl. ..... 250/343; 250/373; 356/436; 356/437

[58] Field of Search ..... 250/343, 373; 356/437, 436

[56] References Cited

U.S. PATENT DOCUMENTS

| | | |
|---|---|---|
| 2,212,211 | 8/1940 | Pfund . |
| 3,711,708 | 1/1973 | Dolin et al. . |
| 3,735,565 | 5/1973 | Gilby et al. . |
| 3,784,836 | 1/1974 | Tolliver . |
| 3,959,660 | 5/1976 | Tolliver . |
| 4,557,603 | 12/1985 | Oehler et al. . |
| 4,587,835 | 5/1986 | Adams . |
| 4,588,893 | 5/1986 | Vidrine et al. . |
| 4,593,197 | 6/1986 | Miyatake et al. . |
| 4,746,218 | 5/1988 | Lord, III . |
| 4,808,825 | 2/1989 | Miyatake et al. . |
| 4,891,518 | 1/1990 | Day . |
| 4,956,759 | 9/1990 | Goldenberg et al. . |
| 4,958,076 | 9/1990 | Bonne et al. . |
| 5,047,006 | 9/1991 | Brandston et al. . |
| 5,054,869 | 10/1991 | Doyle . |
| 5,060,508 | 10/1991 | Wong . |
| 5,065,025 | 11/1991 | Doyle . |
| 5,070,245 | 12/1991 | Rantala et al. . |
| 5,125,742 | 6/1992 | Wilks, Jr. . |
| 5,163,322 | 11/1992 | Wong . |
| 5,254,858 | 10/1993 | Wolfman et al. . |
| 5,317,897 | 6/1994 | Jelley et al. . |
| 5,457,523 | 10/1995 | Tobias ..... 356/300 |

FOREIGN PATENT DOCUMENTS

| | | |
|---|---|---|
| 60-149949 | 8/1985 | Japan . |
| 63-103939 | 5/1988 | Japan . |

OTHER PUBLICATIONS

Paul A. Wilks, "IR analyzers for ambient air and process stream monitoring," *American Laboratory*, pp. 26C–26E, Oct. 1991.

Donald E. Williamson, "Cone Channel Condenser Optics," *Journal of the Optical Society of America*, vol. 42, No. 10, pp. 712–715, Oct. 1952.

*Primary Examiner*—Constantine Hannaher
*Attorney, Agent, or Firm*—Herbert M. Wolfson

[57] ABSTRACT

A spectral analyzer has a high efficiency optical collector having a first concave reflector portion and an opposed second concave reflector portion providing an exit passage therethrough, and a light emitting source of a predetermined wavelength range is positioned in the collector so that the light is collected and directed to the exit passage. A specimen holder is positioned adjacent the exit passage and has windows at its entrance and exit ends. An elongated reverse non-imaging optical member which has a peripheral wall reflecting light rays entering through the exit window of the holder reduces the angle of the rays relative to the optical axis of the optical member as they pass therethrough. The light passing through the exit end of the optical member enters a detector assembly including at least one photo detector sensitive to a predetermined wavelength of light, and at least one optical filter disposed between the optical member and the photodetector to pass light of the predetermined wavelength.

23 Claims, 9 Drawing Sheets

SPECTRAL ANALYZER WITH NEW HIGH EFFICIENCY COLLECTION OPTICS AND METHOD OF USING SAME

Matter enclosed in heavy brackets [ ] appears in the original patent but forms no part of this reissue specification; matter printed in italics indicates the additions made by reissue.

BACKGROUND OF THE INVENTION

The present invention relates to a spectral analyzer and, more particularly to an improved spectral analyzer which is adapted for measurement of multiple components of a specimen.

Spectroscopic analyzers are now widely employed in the analysis of various types of specimens including gases, solids and liquids. This is done by employing specimen holders or light guides of different types to enable absorption or modification of light transmitted therethrough or absorbed at an interface with the specimen. Although many analyzers are designed to operate and measure the effect of a specimen upon light rays of a single wavelength band, some employ two or three photodetectors to concurrently measure the several different components.

Although the infrared wavelength is most widely utilized, it is also possible to use light rays in the ultraviolet wavelength, in the visible light wavelength, and even broad band light rays depending upon the specimen and the components thereof which are being analyzed, particularly when suitable filters are used in the apparatus.

Some of the problems experienced with existing analyzers include relatively low signal to noise ratio and poor collection efficiency. As a result, relatively long cells for gaseous and other specimens are required.

It is an object of the present invention to provide a novel spectral analyzer which is highly efficient and small in size.

It is also an object to provide such a spectral analyzer which is adaptable for use with gaseous, solid and liquid specimens.

Another object is to provide such an analyzer which may be used to analyze simultaneously a multiplicity of components of a specimen.

A further object is to provide such a spectral analyzer which is adaptable to measure diffuse and specular reflectance of solids.

A still further object is to provide a novel method for spectral analysis using such a spectral analyzer.

SUMMARY OF THE INVENTION

It has now been found that the foregoing and related objects may be readily attained in a spectral analyzer which includes a high efficiency optical collector having a first concave reflector portion and an opposed second concave reflector portion with an exit passage therethrough. A source for light emitting of a predetermined wavelength range is positioned in the collector so that the emitted light is collected and directed by the reflector portions to the exit passage. A specimen holder is positioned adjacent the exit passage of the collector, and it has entrance and exit ends with windows therein.

At the exit end of the specimen holder is the entrance end of an elongated reverse non-imaging optical member. This optical member has a peripheral wall reflecting light rays entering it through the exit window of the holder to reduce the angle of the rays relative to the optical axis of the optical member as they pass therethrough. At the exit end of the optical member is a detector assembly including at least one photodetector sensitive to a predetermined wavelength of light and at least one optical filter disposed between the optical member and the photodetector to pass light of the predetermined wavelength.

Preferably, the first portion of the collector may conveniently be a concave spherical surface or an ellipsoidal surface.

Desirably, the reverse non-imaging optical member has a compound parabolic configuration, although it may also have a configuration selected from the group of general conics, aspheres and splines.

Preferably, the windows of the specimen holder filter a frequency or pass a frequency of a predetermined wavelength range. The detector assembly includes an optical concentrator between the filter and the photodetector. Desirably, a multiplicity of cooperating photodetectors and cooperating filters sensitive to light rays of different wavelength ranges is provided in the detector assembly.

The specimen holder may be a tubular element for containing a gas or include means for supporting a translucent solid specimen, or include means for locating the surface of a specimen at an angle to the longitudinal axis of the holder. The specimen holder may also be a solid translucent light guide which permits evanescent spectral energy absorption at the interface with a specimen disposed on its periphery.

If so desired, a chopper may be provided to pulse the light rays passing into the specimen holder. Moreover, although light rays in the infrared wavelength are generally preferred, ultraviolet and visible light may also be employed.

In use, power is provided to the light source to effect emission of light rays which are collected and reflected to the exit aperture from the collector and into the specimen holder containing a specimen to be analyzed. The specimen interacts with the light rays to provide spectral indicia of the components thereof.

The light rays are then passed through an elongated non-imaging optical member to reduce the angle of the light rays entering thereinto relative to the optical axis of the optical member. The light rays exiting the optical member then impinge upon a photodetector to generate signals indicative of a component of the specimen, and these signals from the photodetector are analyzed.

As previously described, preferably the light rays exiting the optical member are directed through a filter prior to impinging upon the photodetector, and the light rays exiting the optical member are directed through an optical concentrator,prior to the photodetector.

DETAILED DESCRIPTION OF THE PREFERRED EMBODIMENT

Figure 1:
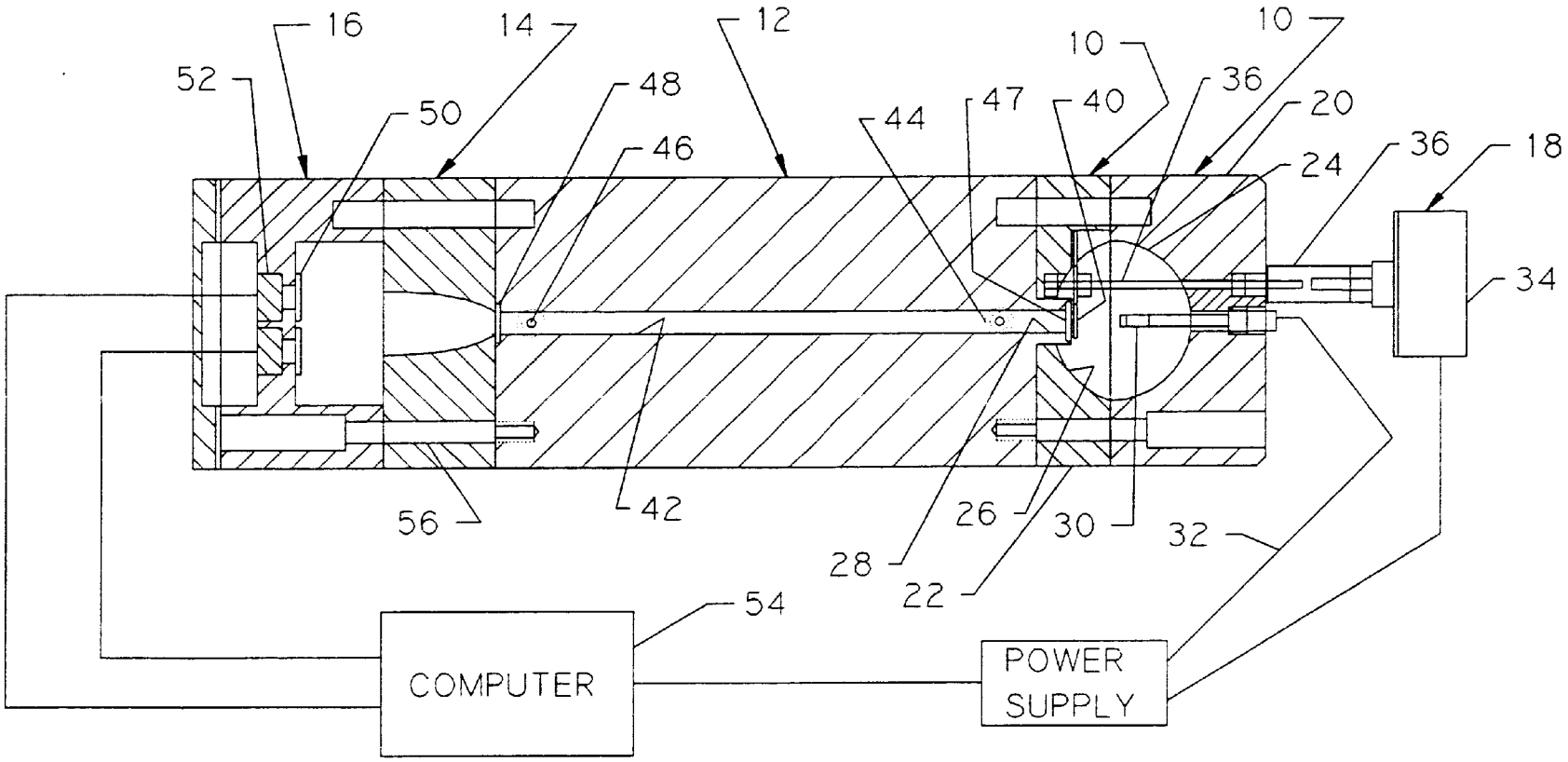
FIG. 1 is a partially diagrammatic view of a spectral analyzer for gases and liquids embodying the present invention.
Figure 2:
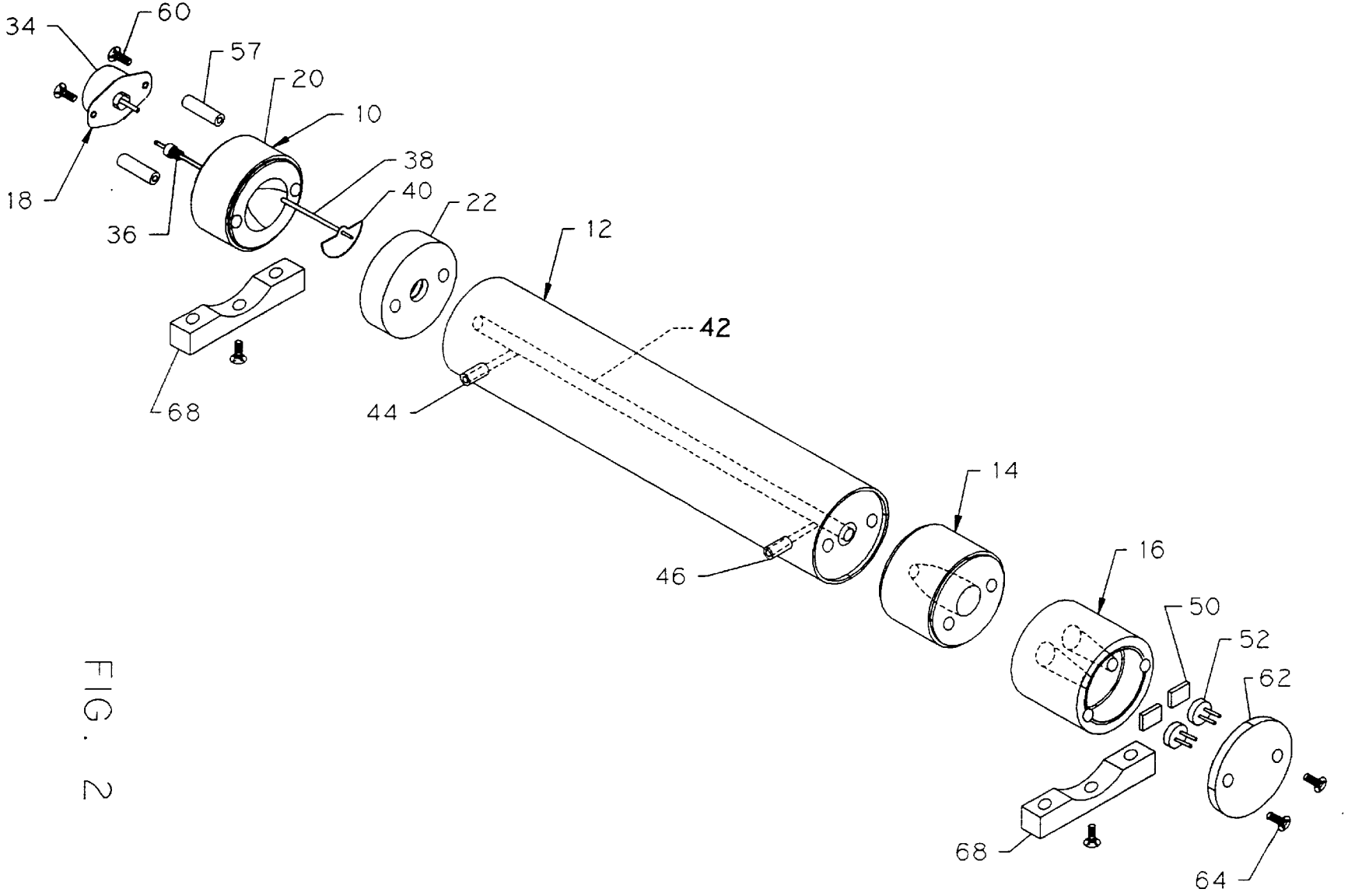
FIG. 2 is an exploded view of the analyzer of FIG. 1.

Turning first to FIGS. 1 and 2, therein diagrammatically illustrated is an analyzer embodying the present invention and generally comprised of a light source and collector generally designated by the numeral 10, a specimen holder generally designated by the numeral 12, a reverse non-imaging optical member generally designated by the numeral 14, and a detector assembly generally designated by the numeral 16. Also shown is a chopper assembly generally designated by the numeral 18.

The collector 10 is conveniently comprised of a pair of blocks 20 and 22 providing a concave spherical surface 24 and an opposing concave spherical surface 26, respectively. A coaxially disposed aperture 28 is provided in the block 22. A light source 30 is coaxially disposed in he block 20 so that the light rays generated by it will be reflected from the surfaces 24,26 and directed to the aperture 28. The light source or emitter 30 is connected to a power source (not shown) by the cable 32.

The chopper assembly 18 includes a drive motor 34 with a coupling 36 which transmits rotary motion to the drive shaft 38 upon which is mounted the chopper blade 40 which extends across the aperture 28. Power is supplied to the motor 34 through the cable 35.

The specimen holder 12 in this embodiment is adapted for passage of a gas or liquid therethrough and comprises a block having a coaxial cavity 42 therein. Inlet and outlet ports 44 and 46 allow flow therethrough of the gas or liquid to be analyzed, and the windows 47,48 at each end thereof retain the gas or liquid therein.

After passage through the specimen in the holder 12, the light rays exit through the window 48 into the non-imaging optical member 14. As the light rays pass therethrough, they are reflected from the wall surface defining the passage 50 so that they exit at angles which are smaller relative to the optical axis of the passage 50, i.e., they are travelling more closely to the optical axis.

Upon exiting the optical member 14, the light rays pass into detector assembly 16 where they pass through filters 52 and are incident upon the photodetectors 54 which measure the intensity of the filtered light rays. Signals are outputted through the leads 55 to a computer 56 which interprets the intensity to determine concentration of the components being analyzed.

As more specifically illustrated in FIG. 2, a convenient assembly is provided by the several blocks and tubes which are joined by pins or dowels 57 seated in aligned recesses 58 and secured therein by adhesive, friction or set screws. A flange on the chopper motor 34 is secured to the block 20 by threaded fasteners 60. A removable end cap 62 is secured by fasteners 64 to the block 66 which provides the housing of the detector assembly 16. This entire assembly is supported on mounts 68 which may be secured to any suitable support (not shown).

Figure 3:
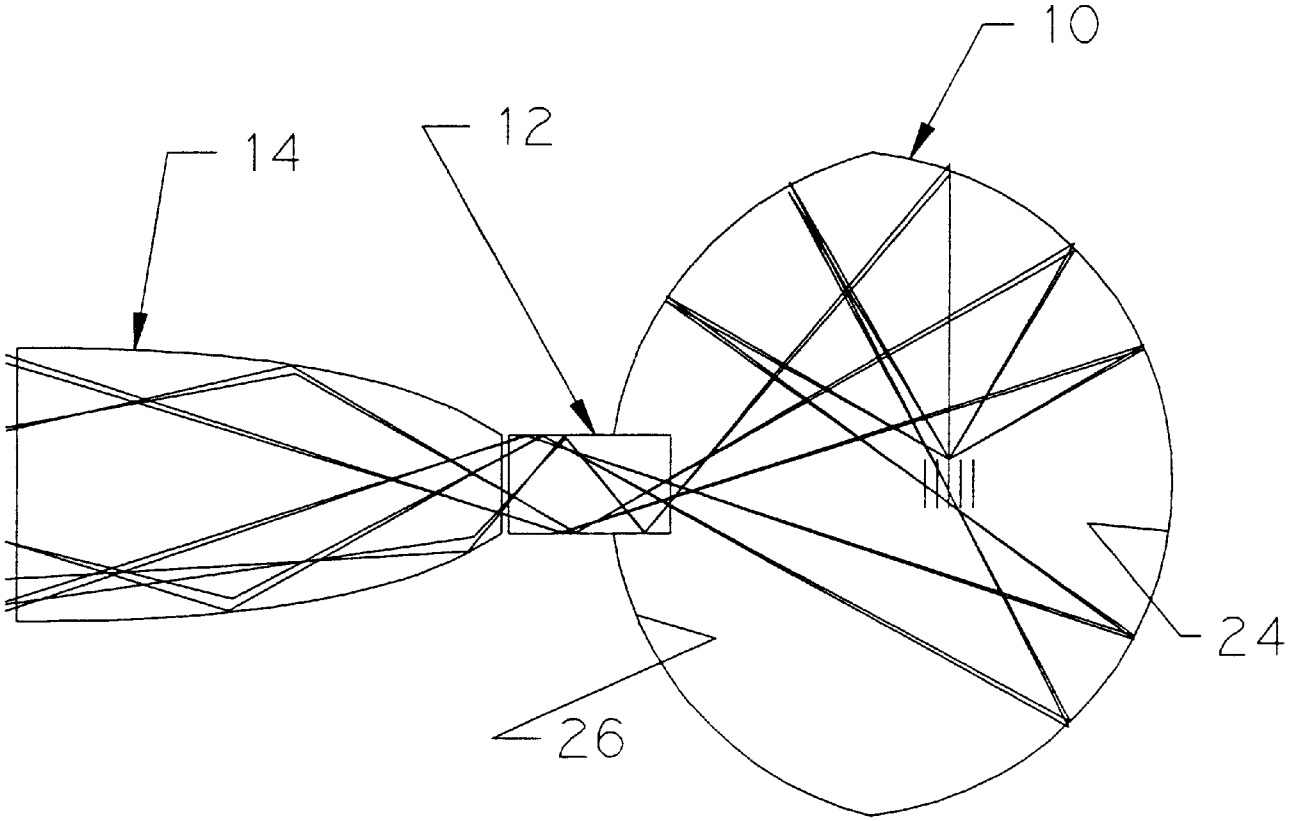
FIG. 3 is a diagrammatic view of the collector, gas cell and parabolic concentrator showing traces of the light rays passing therethrough.

Turning next to FIG. 3, therein schematically illustrated are ray traces showing light rays emitted by the source 30 being reflected by the surfaces 24, 26 to the exit aperture 28 which extends to the window 28 (seen in FIG. 1) and thence into the specimen holder 12. The light rays are reflected from its surfaces and pass therethrough and through the specimen contained therein until they exit the holder 12 and pass into the non-imaging optical member 14. The light rays are reflected from the surface defining the passage through the member 14 so that they exit at a relatively shallow angle relative to the optical axis 72 of the assembly.

Figure 4A:
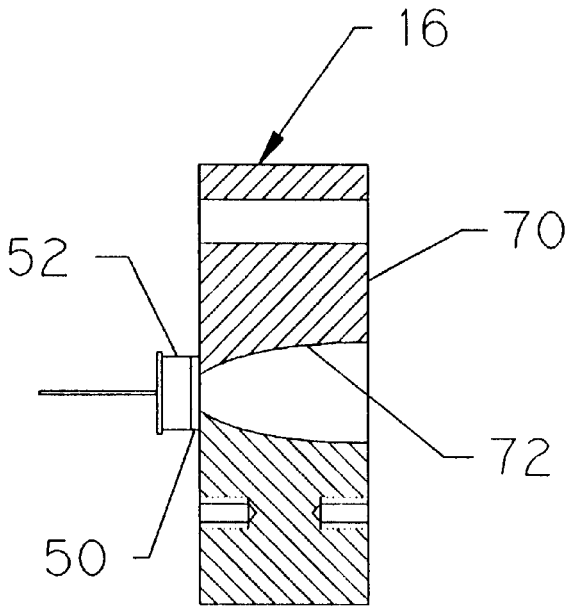
FIGS. 4a and 4b are partially diagrammatic view of a ray concentrator for the detector assembly to concentrate rays impinging upon the photodetectors.
Figure 4B:
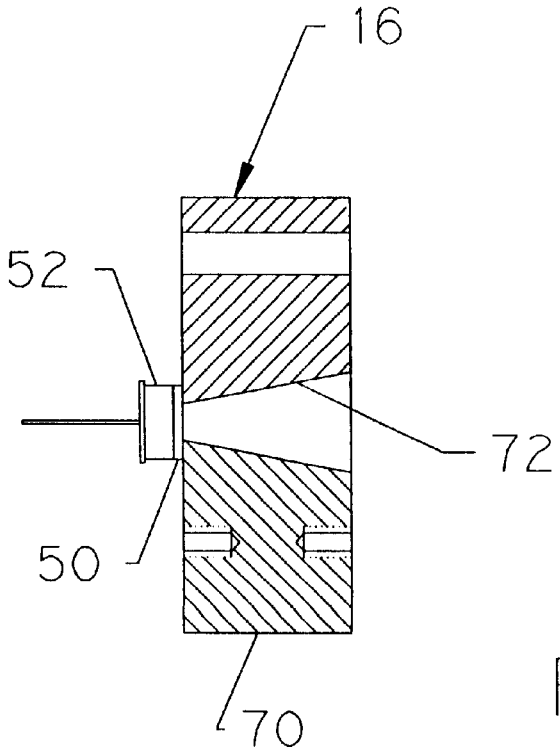

Although not essential, the effectiveness of the apparatus may be increased by including within the detector assembly 16 light guides or concentrators to direct light rays onto the photodetectors 52. As seen in FIGS. 4a and 4b, the detector housing 70 may incorporate a plurality of converging passages 72 (only one is shown) which have exit ends aligned with the photodetectors 52.

Figure 5A:
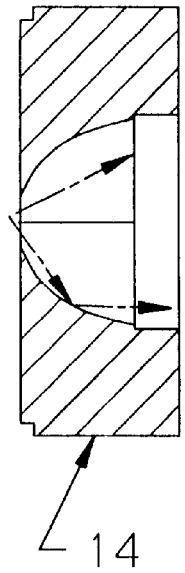
FIG. 5a–5d are diagrammatic views of different configurations of reverse non-imaging optical members which may be utilized in the present invention.
Figure 5B:
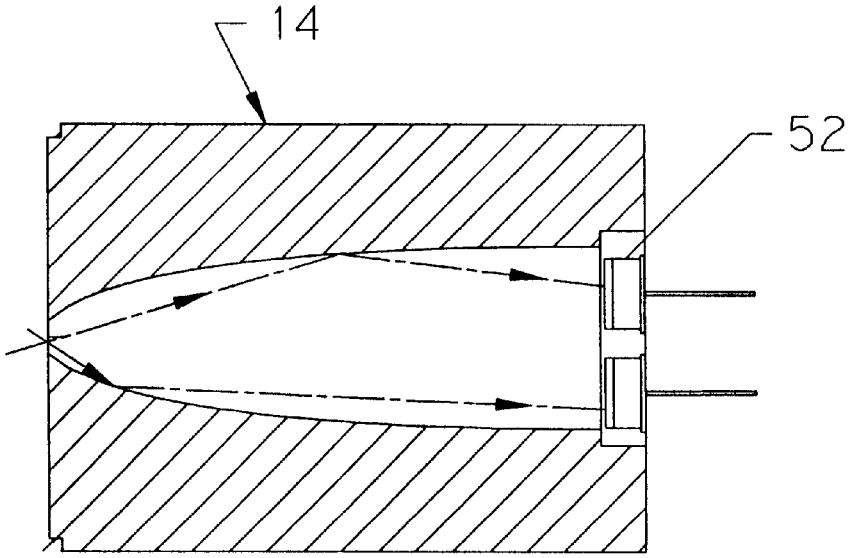
Figure 5C:
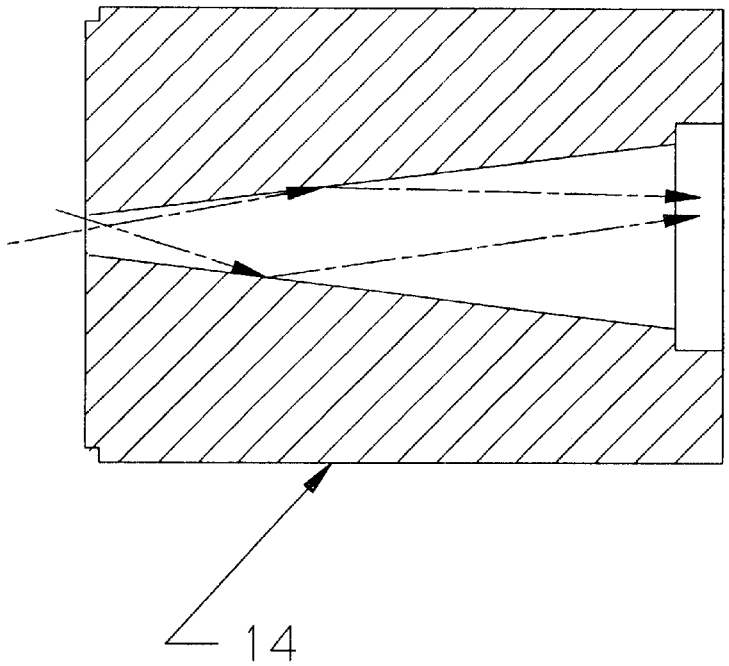
Figure 5D:
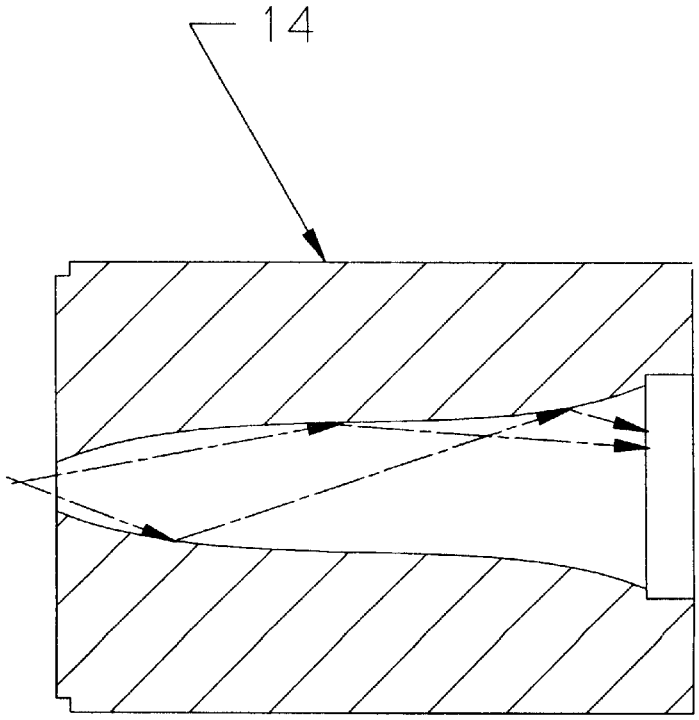

Illustrated diagrammatically in FIGS. 5a–dd are several configurations of reverse non-imaging optical members to reduce the angle of light rays passing therethrough as indicated by the ray traces. FIGS. 5a and 5b are other types of aspheric surfaces; FIG. 5c shows a conic surface; and FIG. 5d shows use of the surface of a spline.

Figure 6A:
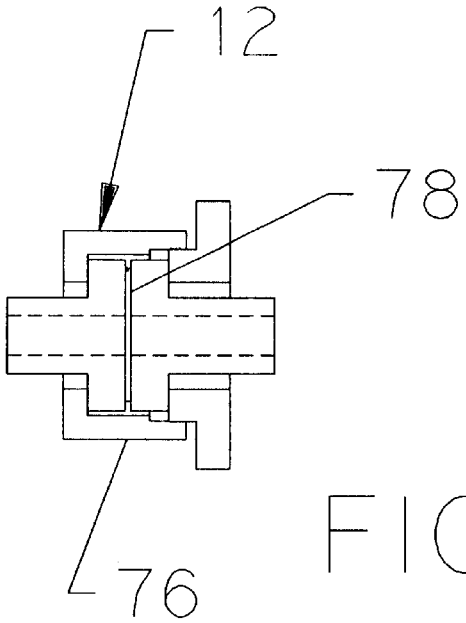
FIG. 6a–6c are diagrammatic views of other types of specimen holders which may be used.
Figure 6C:
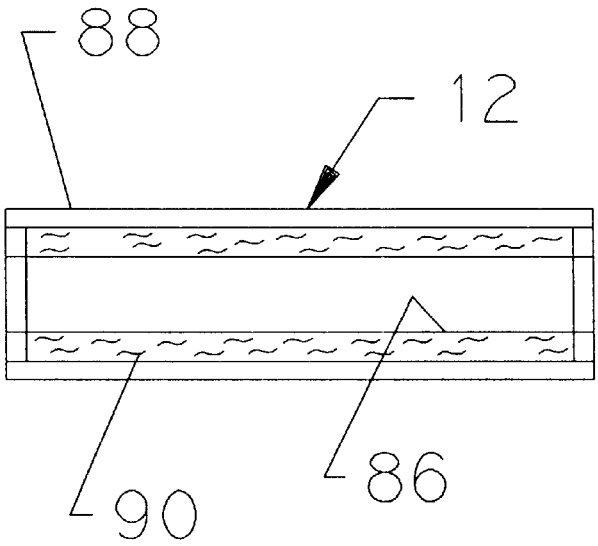
Figure 6B:
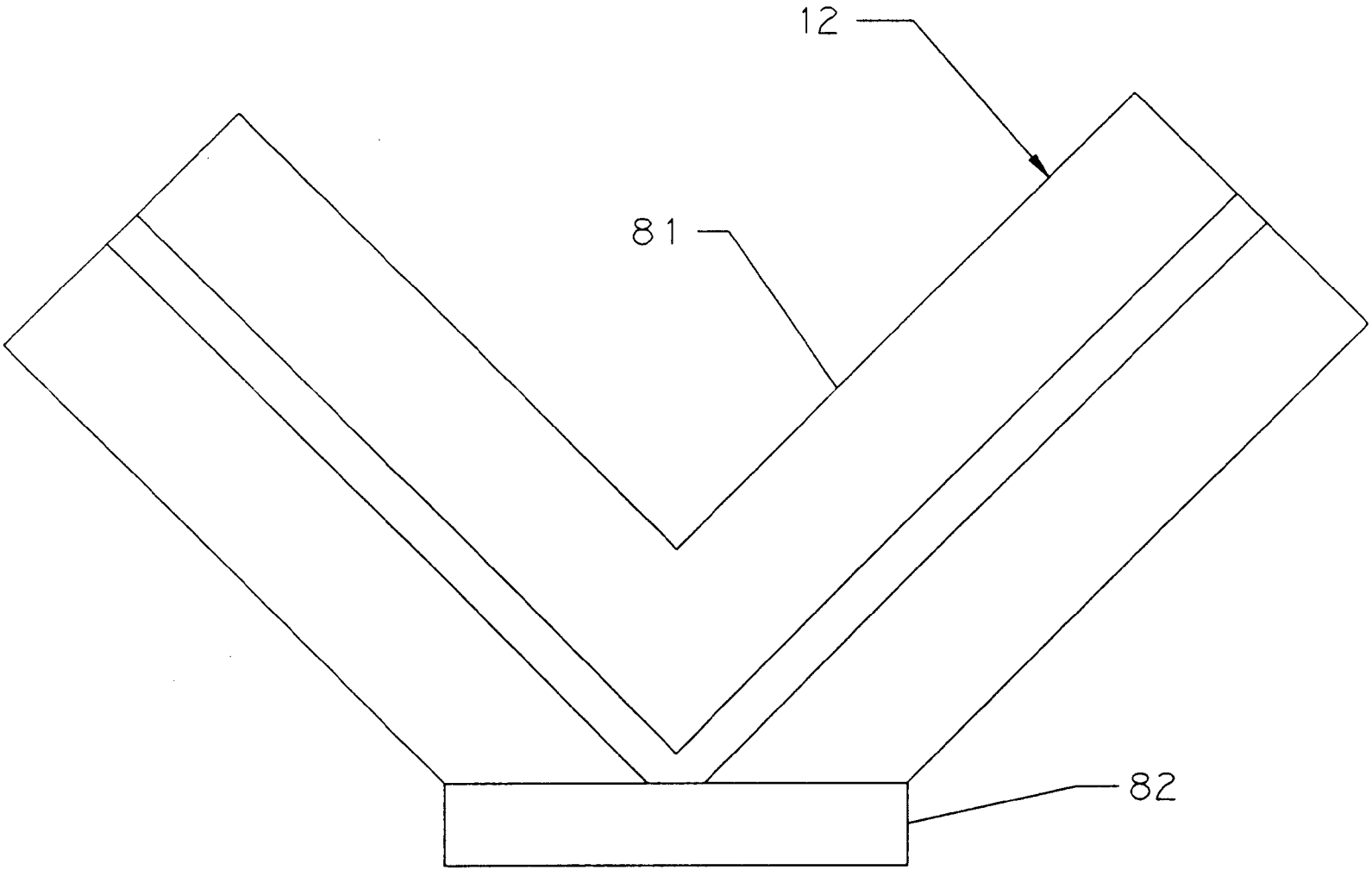

As seen in FIGS. 6a–6c, the specimen holder may have a number of constructions depending upon the type of material being analyzed, and the nature of the action of the specimen on the light rays, e.g, absorption, reflection and evanescence.

The embodiment illustrated in FIGS. 1 and 2 uses a specimen holder in which the light rays are transmitted through the specimen and is generally adapted for use with liquids and gases. FIG. 6a illustrates a specimen holder 76 for a translucent solid specimen 78 through which the light rays are transmitted. FIG. 6b illustrates a holder 80 for an opaque solid providing a V-shaped light guide 81 which has the specimen 82 supporting at its apex so that the light rays are reflected from its surface. FIG. 6c illustrates a specimen holder 84 in which the light guide 86 extends through a tube 88 containing a liquid specimen 90 and attenuation at the surface of the light guide 86 is effected.

As previously described, the light rays exiting the non-imaging optical member desirably pass through filters which cooperate with an associated photodetector. These filters may allow only a light of narrow wavelength range to pass therethrough or may selectively remove light of a narrow range depending upon the band wavelength(s) being measured by the detector.

As a direct result of the optics the light rays are directed at angles approaching normal to the filter and the spectral filters are able to function more efficiently in the effort to analyze the optical energy after its interaction with the sample. The filters are typically designed to allow for a specific wavelength band width to pass through the filter while rejecting all other energy. Therefore, if the filters are selected to have a bandwidth which closely matches the absorption band of the sample in the compartment, they will be able to alert the system to the absence of optical energy which is of a wavelength synonymous with a particular material. This allows one to identify the presence of some known material in the sample compartment due to its absorption.

Because of its efficiency and compact size, the spectral analyzer of the present invention may be fabricated as a small battery operated gas detection instrument to make possible easy and economical atmospheric monitoring for a wide variety of gases. The components may be fabricated readily and relatively economically so that the cost to the user is relatively small by comparison to existing units which are much larger, heavier and not truly portable. Two components may be combined such as the non-imaging optical member and detector assembly as seen in FIG. 5d.

The light collection and channelling properties of the present invention are highly efficient, and the components may be designed so as to permit modular manufacturing and assembly of the three major components (source/collector, specimen holder, energy collector/re-director) into a multitude of geometries. The light collecting and channeling efficiency of the present invention has industrial applicability in gas analysis, fluid analysis, fluorescence analysis and generally any application where spectral information can be obtained by means of sample/optical energy interaction.

Moreover, as a result of this highly efficient assembly, four or more different components in a specimen may be monitored by providing a series of different photodetectors and cooperating filters, each monitoring light of a different wavelength indicative of the different components.

In the optical collector, the two reflective surfaces cooperate with the light emitter placed therebetween. In the optical system described above, the components are arranged so as to allow for maximum solid angle radiometric efficiency.

The relationship of focal points and overall geometry of the collecting optic shells defines their collection efficiency. The first half of the optical shell has its vertex located behind the centerpoint of the optical source. This particular section may have one of two general geometries. The first is the simple sphere. The radius of the sphere is selected so as to produce an image of the source at the window to the specimen holder.

Figure 7:
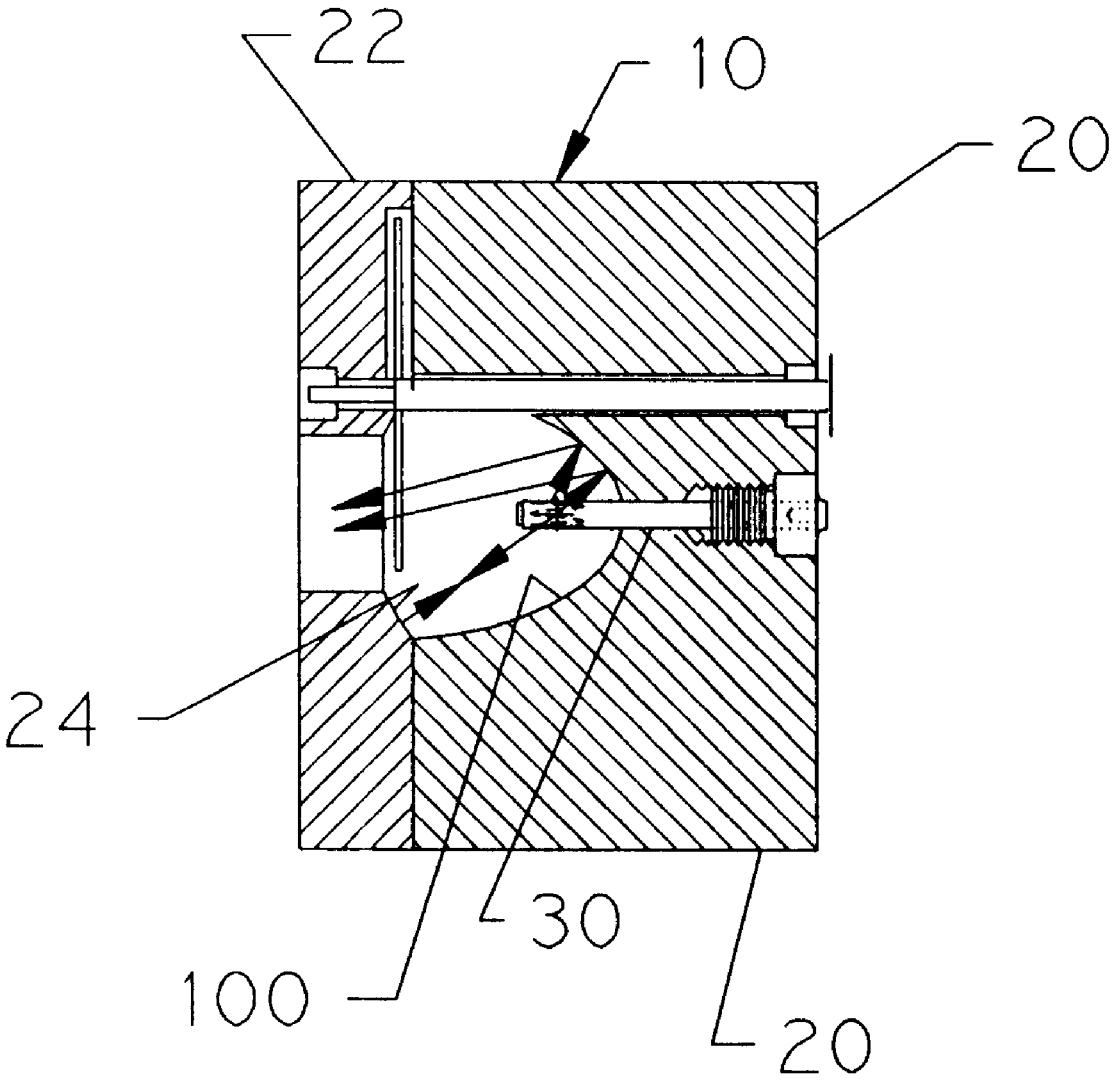
FIG. 7 is a diagrammatic view of a collector having parabolic and spherical reflection surfaces.

Another option for the geometry of the first block 20 section is an ellipsoidal surface 100 seen in FIG. 7. In this case, the ellipsoid would have one focus located at D1 and the other at D2. The advantage to utilizing an ellipsoid over a sphere is the reduction of aberrations such as spherical aberration encountered when utilizing a sphere in this manner. However, so long as the blur diameter resulting from the spherical mirror is equal to or smaller than the diameter of the sample compartment, aberrations may be neglected. The chief disadvantage to utilizing an aspherical (ellipsoid or variation of an ellipsoid with additional deformations to allow for aberration correction) is the associated higher manufacturing costs.

The second portion of the collecting optics should always take the form of a sphere. This spherical mirror will be positioned with its center of curvature coaxial with the center of the emitter. The result of such an arrangement is that all energy which exceeds the acceptance of the first shell half, will reflect from the second shell half and return towards a section of the first shell portion which allows for the energy to be focused into the specimen holder, as seen in FIG. 3.

In the embodiment shown in FIG. 1, the emitter may be an infrared (IR) energy source which can be the equivalent of a heated wire operating at 660°–800° C. This gives a broad band of IR radiation from 2–15 microns which is collected into a narrow beam of IR energy by the reflective surfaces. As seen in FIG. 3, the collection of light from a finite source by the mirror segment up to NA (numerical aperture) of 1.0+ is focused into the entrance aperture of the specimen holder. The collection efficiency is increased beyond 1.0+ NA by the addition of the second concave collecting optic which redirects the energy from angles exceeding the 1.0+ NA condition, towards the focus of the first mirror segment. Thus, the first segment can re-collect this energy and direct it to the entrance aperture of the specimen holder. Therefore, the collector optics ensure a high collection ratio of energy from the emitter.

The specimen will encode the incident optical energy with information regarding its molecular physical properties. As is known, optical energy of particular specular characteristics will be affected by the specimen composition. Therefore, the optical energy emergent from the specimen holder will carry with it information which indicates the molecular nature of the specimen.

The windows for the specimen holder desirably utilize materials which allow the transmission of optical energy which falls within the optical wavelength bandwidth of interest. For instance, windows would be comprised of barium fluoride for an infrared detection apparatus. This material is selected due to its ability to transmit IR energy with no absorption in the regions of interest to the analysis.

As previously indicated, the reverse non-imaging optical member is of a geometry which reduces the angle of incident rays as they traverse its length. The concept of these optics can be envisioned as a collection of points which define a tangent to the angle of the light accepted and a lesser angle.

As a result of the angular orientation of the optics, the degree of perpendicularity between the rays exiting the non-imaging optical member and the normal to the optical filter and photodetector is increased. Narrow wavelength band optical filters are designed to allow for transmission of a relatively small selective region of wavelengths. This may be accomplished through the stacking of different layers of transmissive materials. Energy which strikes the surface of the filter at angles departing from the normal to the surface will have a path length in the medium defined by the skew path through a particular filter layer. The greater is this angle, the larger is the error. The filter allows for the transmission of wavelengths which produce a certain pathlength in the medium. The energy of a lesser wavelength which is at a higher angle of incidence on the filter will look to the filter as wavelengths with the proper pathlength. This phenomenon known as "blue shifting" explains how these wavelengths of a lower angle (bluer) are allowed to pass therethrough. Thus, the non-imaging optical member reduces this inherent error. Some typical formulas for "non-imaging" optics can be found in the text: The Optics of Non-Imaging Concentrators by Welford & Winston, published by Academic Press.

Thus, it can be seen from the foregoing detailed specification and attached drawings that the spectral analyzer of the present invention may be readily and economically fabricated, is highly efficient and is sufficiently small and lightweight so as to provide a portable unit for many field applications in addition to serving as a laboratory or industrial unit. The analyzer is adapted for use with gas, solid and liquid specimens by means of readily interchangeable holders, and its efficiency enables dividing the light beam traversing the specimen holder to provide multiple beams directed onto a multiplicity of photodetectors to enable concurrent analysis of multiple components in the specimens.

Having thus described in the invention, what is claimed is:

1. A spectral analyzer comprising:

(a) a high efficiency optical collector having a first concave reflector portion and an opposed second concave reflector portion, said second reflector portion having an exit passage therethrough;

(b) a source for light emitting of a predetermined wavelength range positioned in said collector so that the emitted light is collected and directed by said reflector portions to said exit passage;

(c) a specimen holder positioned adjacent said exit passage of said collector and having entrance and exit ends;

(d) an elongated non-imaging optical member having its entrance end at the exit end of said specimen holder and having an exit end, said member having a peripheral wall reflecting light rays entering through the exit end of said holder to reduce the angle of the rays relative to the optical axis of said optical member as they pass therethrough; and (e) a detector assembly at the exit end of said optical member including at least one photodetector sensitive to a predetermined wavelength of light and at least one optical filter disposed between said optical member and said detector to pass light of said predetermined wavelength.

2. The spectral analyzer in accordance with claim 1 wherein said second portion of said collector is a concave spherical surface.

3. The spectral analyzer in accordance with claim 1 wherein said first portion of said collector is a concave spherical surface.

4. The spectral analyzer in accordance with claim 1 wherein said first portion of said collector is an ellipsoidal surface.

5. The spectral analyzer in accordance with claim 1 wherein said non-imaging optical member has a compound parabolic configuration.

6. The spectral analyzer in accordance with claim 1 wherein said non-imaging optical member has a configuration selected from the group consisting of conical, generally aspherical and spline.

7. The spectral analyzer in accordance with claim 1 wherein said entrance and exit ends of said specimen holder have windows therein to filter light rays to pass those of a predetermined wavelength range.

8. The spectral analyzer in accordance with claim 1 wherein said detector assembly includes an optical concentrator between said filter and said photodetector.

9. The spectral analyzer in accordance with claim 1 wherein a multiplicity of cooperating photodetectors and a multiplicity of cooperating filters sensitive to light rays of different wavelength ranges are provided in said detector assembly.

10. The spectral analyzer in accordance with claim 1 wherein said specimen holder provides a chamber for receiving the specimen and through which the light rays will pass.

11. The spectral analyzer in accordance with claim 1 wherein said specimen holder includes means for supporting a translucent solid specimen.

12. The spectral analyzer in accordance with claim 1 wherein said specimen holder includes means for locating the surface of a specimen at an angle to the longitudinal axis of said holder.

13. The spectral analyzer in accordance with claim 1 wherein said specimen holder is a solid translucent light guide which permits evanescent spectral energy absorption at the interface with a specimen disposed on its periphery.

14. The spectral analyzer in accordance with claim 1 wherein there is included a chopper to pulse the light rays passing into said specimen holder from said collector.

15. The spectral analyzer in accordance with claim 1 wherein said light source emits light rays in the infrared wavelength.

16. The spectral analyzer in accordance with claim 1 wherein said light source includes means for pulsing said source.

17. The spectral analyzer in accordance with claim 1 wherein said light emitting source emits light of a broad range of wavelength range.

18. In a method for spectral analysis, the steps comprising:

(a) providing a source of light of a predetermined wavelength range within a collector having opposed concave reflective surfaces;

(b) providing power to said light source to effect emission of light rays;

(c) collecting and reflecting said light rays to an exit aperture from said collector and into a specimen holder containing a specimen to be analyzed, said specimen interacting with said light rays to provide a spectral indicia of components therein;

(d) passing the light rays through an elongated non-imaging optical member to reduce the angle of the light rays entering thereinto relative to the optical axis of said member;

(e) directing the light rays exiting said optical member onto a photodetector to generate signals indicative of a component of said specimen; and (f) analyzing said signals from said photodetector.

19. The method of spectral analysis in accordance with claim 18 wherein said light rays exiting said optical member are directed through a filter prior to impinging upon said photodetector.

20. The method of spectral analysis in accordance with claim 18 wherein said light rays exiting said optical member are directed through an optical concentrator prior to said photodetector.

21. The method of spectral analysis in accordance with claim 18 wherein windows are provided at the entrance and exit ends of said specimen holder to filter the light rays passing therethrough.

*22. A spectral analyzer comprising:*

*(a) a source of light capable of emitting a predetermined wavelength range directed to an exit passage;*

*(b) a specimen holder positioned adjacent said exit passage having entrance and exit ends;*

*(c) an elongated non-imaging member having its entrance end at the exit end of said specimen holder and having an exit end, said elongated member having a peripheral wall adapted to reflect light rays emitted from said exit end of said specimen holder to reduce the angle of such rays relative to the optical axis of said elongated member as said light rays pass therethrough; and*

*(d) a detector assembly at said exit end of said elongated member including at least one photodetector sensitive to a predetermined wavelength of light and at least one optical filter disposed between said elongated member and said detector assembly adapted to pass light of said predetermined wavelength.*

*23. In a method for spectral analysis, the steps comprising:*

*(a) providing a source of light of a predetermined wavelength range;*

*(b) providing power to said light source to effect emission of light rays into a specimen holder containing a specimen to be analyzed, said specimen interacting with said light rays to provide a spectral indicia of components therein;*

*(c) directing the light rays exiting said specimen holder through an elongated non-imaging member adapted to reflect said light rays to reduce their angle relative to the optical, axis of elongated member and onto a photodetector to generate signals indicative of a components of said specimen; and*

*(d) analyzing said signals from said photodetector.*

* * * * *